United States Patent
Mazzoleni et al.

(10) Patent No.: US 12,370,407 B2
(45) Date of Patent: *Jul. 29, 2025

(54) FITNESS TRACKING SYSTEM AND METHOD OF OPERATING A FITNESS TRACKING SYSTEM

(71) Applicant: Under Armour, Inc., Baltimore, MD (US)

(72) Inventors: Michael Mazzoleni, Baltimore, MD (US); F. Grant Kovach, Baltimore, MD (US); Jeffrey Allen, Baltimore, MD (US); John Martin, Baltimore, MD (US); Daniel Sargeant, Baltimore, MD (US); Bradford J. Fults, Baltimore, MD (US); Chirstopher Green, Baltimore, MD (US); Mark Oleson, Baltimore, MD (US); Nathan Dau, Baltimore, MD (US)

(73) Assignee: Under Armour, Inc., Baltimore, MD (US)

( * ) Notice: Subject to any disclaimer, the term of this patent is extended or adjusted under 35 U.S.C. 154(b) by 1036 days.

This patent is subject to a terminal disclaimer.

(21) Appl. No.: 17/387,522

(22) Filed: Jul. 28, 2021

(65) Prior Publication Data
US 2021/0353234 A1 Nov. 18, 2021

Related U.S. Application Data

(63) Continuation of application No. 16/010,099, filed on Jun. 15, 2018, now Pat. No. 11,076,814.

(51) Int. Cl.
*A63B 24/00* (2006.01)
*A43B 5/06* (2022.01)
(Continued)

(52) U.S. Cl.
CPC ............ *A63B 24/0062* (2013.01); *A43B 5/06* (2013.01); *A61B 5/0004* (2013.01); *A61B 5/0022* (2013.01); *A61B 5/1038* (2013.01); *A61B 5/1112* (2013.01); *A61B 5/1118* (2013.01); *A61B 5/112* (2013.01); *A61B 5/1123* (2013.01); *A61B 5/6807* (2013.01); *A61B 5/7264* (2013.01); *A61B 5/7285* (2013.01); *A61B 2503/10* (2013.01)

(58) Field of Classification Search
CPC ....... G09B 19/00; G06F 3/017; A61B 5/7285; A61B 5/0004; A61B 5/0022; A61B 5/1038; A61B 5/1112; A61B 5/1118; A61B 5/112; A61B 5/1123; A61B 5/6807; A61B 5/7264; A61B 2503/10
See application file for complete search history.

(56) References Cited

U.S. PATENT DOCUMENTS

2014/0335490 A1  11/2014  Baarman et al.
2016/0093199 A1  3/2016   Whitney et al.

*Primary Examiner* — Patrick Fernandes
(74) *Attorney, Agent, or Firm* — Maginot, Moore & Beck, LLP

(57) ABSTRACT

A method of operating a fitness tracking system includes generating movement data corresponding to movement of a user, sampling the generated movement data at a first sampling rate as first sampled data when operating the fitness tracking system in an activity detection mode, and sampling the generated movement data at a second sampling rate as second sampled data when operating the fitness tracking system in a workout mode. The second sampling rate is greater than the first sampling rate.

19 Claims, 7 Drawing Sheets

(51) Int. Cl.
*A61B 5/00* (2006.01)
*A61B 5/103* (2006.01)
*A61B 5/11* (2006.01)

FITNESS TRACKING SYSTEM AND METHOD OF OPERATING A FITNESS TRACKING SYSTEM

CROSS-REFERENCE TO RELATED APPLICATIONS

This application is a continuation of U.S. patent application Ser. No. 16/010,099, filed Jun. 15, 2018, now U.S. Pat. No. 11,076,814, the entire contents of which are incorporated herein by reference.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD

This disclosure relates to the field of fitness tracking systems and in particular to processing movement data generated by a fitness tracking system to determine automatically the activity level of a user of the fitness tracking system.

BACKGROUND

Active individuals, such as walkers, runners, and other athletes commonly use fitness tracking systems to collect and track activity data. For example, runners, walkers, cyclists, and swimmers may utilize a fitness tracking system to determine the distance, duration, and intensity of a workout.

Known fitness tracking systems require the user to provide an input to the fitness tracking system to start storing activity data at the beginning of a workout. These systems also require the user to input data to the fitness tracking system to stop storing activity data at the end of the workout. If the user forgets to provide either of these inputs, then user cannot properly evaluate the workout. For example, if the user forgets to cause the fitness tracking system to start storing activity data, then no activity data are generated during the workout and the user cannot evaluate the workout. Moreover, if the user forgets to cause the fitness tracking system to stop storing activity data, then the stored activity data corresponding to the workout becomes corrupt with post-workout activity data that should not have been stored. Accordingly, known fitness tracking systems are reliant upon the user to activate and deactivate the system. Furthermore, known fitness tracking systems are unforgiving to users that forget to either activate or deactivate the system.

Accordingly, improvements in fitness tracking systems and in the processing of the data collected by fitness tracking systems are desirable in order to increase the usefulness and integrity of the collected data and to improve the user experience.

SUMMARY

According to an exemplary embodiment of the disclosure, a method of operating a fitness tracking system, includes generating movement data corresponding to movement of a user, sampling the generated movement data at a first sampling rate as first sampled data when operating the fitness tracking system in an activity detection mode, and sampling the generated movement data at a second sampling rate as second sampled data when operating the fitness tracking system in a workout mode. The second sampling rate is greater than the first sampling rate. The method further includes operating the fitness tracking system in the activity detection mode in response to determining that a cadence of the user determined from the second sampled data satisfies a cadence threshold, operating the fitness tracking system in the activity detection mode in response to determining that (i) the cadence of the user does not satisfy the cadence threshold, and (ii) a ground contact value of the user determined from the second sampled data satisfies a first ground contact threshold. Moreover, the method includes operating the fitness tracking system in the workout mode in response to determining that (i) the cadence of the user does not satisfy the cadence threshold, (ii) the ground contact value of the user does not satisfy the first ground contact threshold, and (iii) the ground contact value of the user satisfies a second ground contact threshold.

According to another exemplary embodiment, a method of operating a fitness tracking system includes generating movement data corresponding to movement of a user, sampling the generated movement data at a first sampling rate as first sampled data when operating the fitness tracking system in an activity detection mode, and sampling the generated movement data at a second sampling rate as second sampled data when operating the fitness tracking system in a pre-workout mode or a workout mode. The second sampling rate is greater than the first sampling rate. The method further includes switching from operating the fitness tracking system in the pre-workout mode to operating the fitness tracking system in the workout mode in response to determining that (i) a cadence of the user determined from the second sampled data does not satisfy a cadence threshold, (ii) a ground contact value of the user determined from the second sampled data does not satisfy a first ground contact threshold, and (iii) the ground contact value of the user satisfies a second ground contact threshold.

According to yet another exemplary embodiment, a fitness tracking system includes a shoe, a movement sensor, and a controller. The movement sensor is mounted to the shoe and is configured to generate movement data corresponding to movement of a user. The controller is mounted to the shoe and configured to sample the generated movement data at a first sampling rate as first sampled data when the fitness tracking system is operated in an activity detection mode and to sample the generated movement data at a second sampling rate as second sampled data when the fitness tracking system is operated in a pre-workout mode or a workout mode. The second sampling rate is greater than the first sampling rate. The controller is configured to switch the fitness tracking system from operating in the pre-workout mode to operating in the workout mode in response to a cadence of the user satisfying a cadence condition and a ground contact value of the user satisfying a ground contact condition.

BRIEF DESCRIPTION OF THE FIGURES

The above-described features and advantages, as well as others, should become more readily apparent to those of ordinary skill in the art by reference to the following detailed description and the accompanying figures in which.

All Figures © Under Armour, Inc. 2018. All rights reserved.

DETAILED DESCRIPTION

Disclosed embodiments include systems, apparatus, methods and storage medium associated with processing data generated by a fitness tracking system, which is also referred to herein as an activity tracking system.

Aspects of the disclosure are disclosed in the accompanying description. Alternate embodiments of the disclosure and their equivalents may be devised without parting from the spirit or scope of the disclosure. It should be noted that any description herein regarding "one embodiment," "an embodiment," "an exemplary embodiment," and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may or may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

Figure 1:
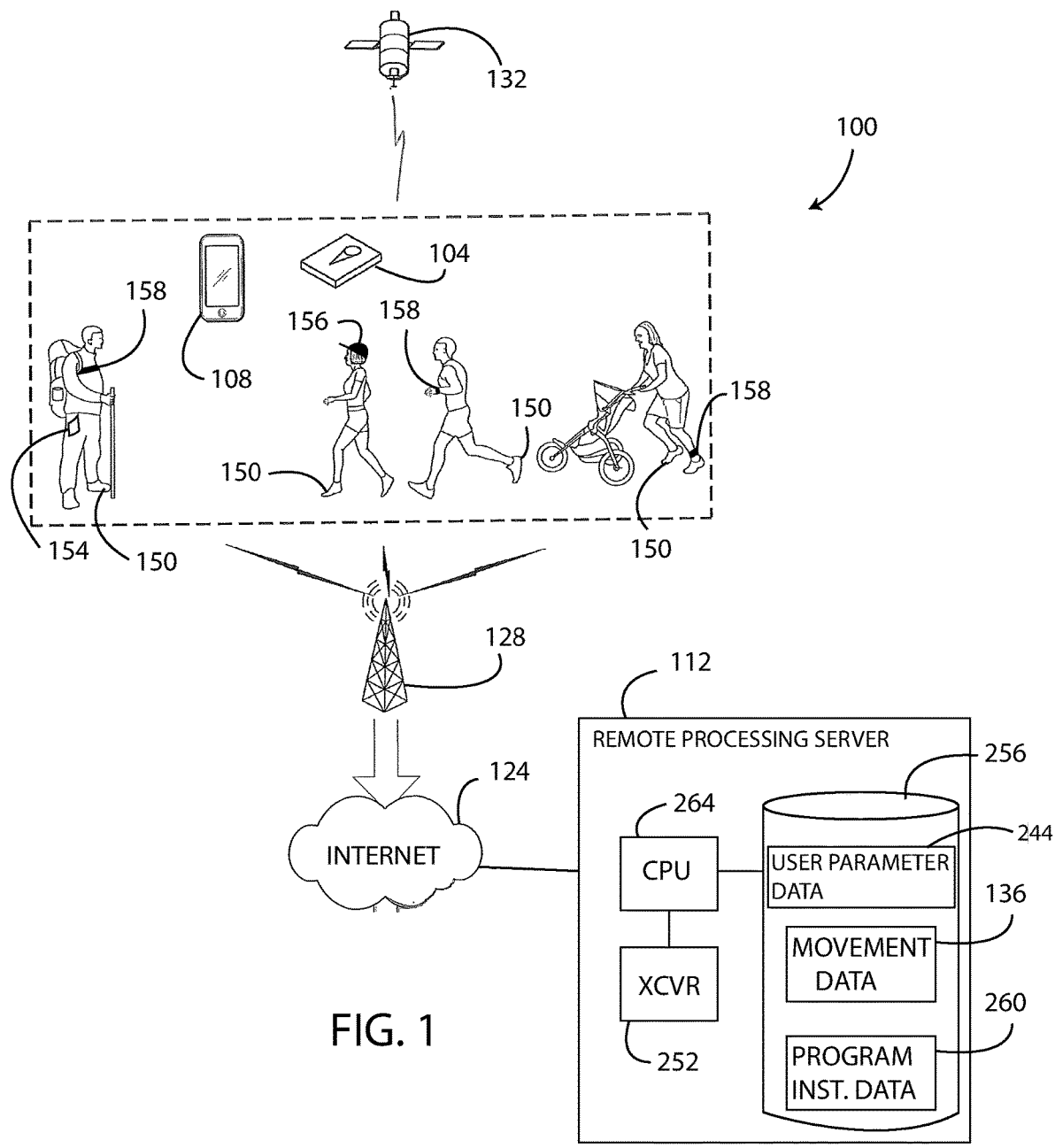
FIG. 1 is a block diagram of a fitness tracking system, as disclosed herein, that includes a monitoring device, a personal electronic device, and a remote processing server.

As shown in FIG. 1, a fitness tracking system 100 includes a monitoring device 104, a personal electronic device 108, and a remote processing server 112. The fitness tracking system 100 is configured to transmit and receive data over the Internet 124 using a cellular network 128, for example. The fitness tracking system 100 may also be configured for use with a global positioning system ("GPS") 132.

As disclosed herein, the fitness tracking system 100 generates movement data 136 corresponding to movement of the user with at least one of the monitoring device 104 and the personal electronic device 108. The fitness tracking system 100 processes at least the movement data 136 to determine automatically if the fitness tracking system 100 should be operated in an activity detection mode, a pre-workout mode, or a workout mode. Components of the fitness tracking system 100 and a method 400 (FIG. 4) for operating the fitness tracking system 100 are described herein.

The Monitoring Device

The monitoring device 104, as shown in FIG. 1, is configured to be worn or carried by a user of the fitness tracking system 100. The monitoring device 104 is mounted on a shoe 150 worn by the user. In one embodiment, the monitoring device 104 is permanently embedded in a sole of the shoe 150, such that the monitoring device 104 cannot be removed from the shoe 150 without destroying the shoe 150. In another embodiment, the monitoring device 104 is configured for removable placement in the shoe 150 (e.g. in a pocket of the shoe 150) and/or is removably attached to the shoe 150. Moreover, the fitness tracking system 100 may include a left monitoring device 104 mounted to the user's left shoe 150 and a right monitoring device 104 mounted to the user's right shoe 150; both monitoring devices 104 are configured identically or substantially identically.

In other embodiments, the monitoring device 104 is carried in a pocket 154 of the user's clothing, is mounted to a hat 156 worn by the user, and/or is mounted to any portion of the user or the user's clothing or accessories (e.g., wrist band, eyeglasses, necklace, visor, etc.). Accordingly, the monitoring device 104 may include a strap 158 to mount the monitoring device 104 onto at least one of the user and the user's clothing. For example, the monitoring device 104 is configured to be strapped to the user's wrist, arm, ankle, or chest. Additionally or alternatively, the strap 158 and the monitoring device 104 are provided as a watch or a watch-like electronic device.

The monitoring device 104, in a further embodiment, is included in a heartrate monitoring device (not shown) that is worn around the wrist, arm, ankle, chest, or other body location that is typically used to measure heartrate.

Figure 2:
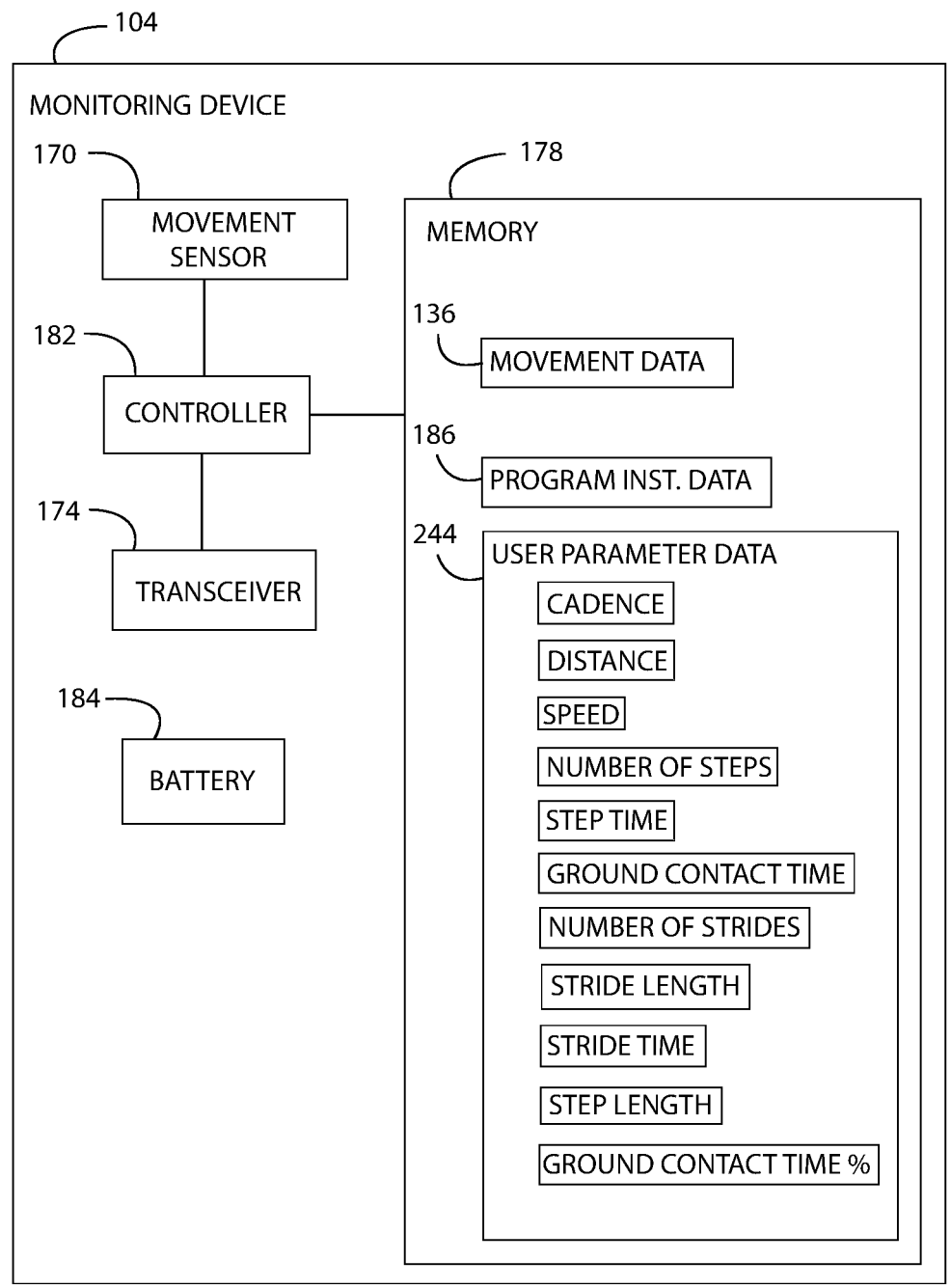
FIG. 2 is a block diagram of the monitoring device of the fitness tracking system shown in FIG. 1.

The monitoring device 104 is configured for mounting (permanently or removably) on any element of the user or the user's clothing, footwear, or other article of apparel using any of various mounting means such as adhesives, stitching, pockets, or any of various other mounting means. The monitoring device 104 is also referred to herein as a measuring device, a health parameter monitoring/measuring device, a distance monitoring/measuring device, a speed monitoring/measuring device, and/or an activity monitoring device As shown in FIG. 2, the monitoring device 104 includes a movement sensor 170, a transceiver 174, and a memory 178 each of which is operably connected to a controller 182 and a battery 184. The movement sensor 170 is configured to generate movement data 136. The term "movement data," as used herein, corresponds to data generated by the movement sensor 170 as a result of movement of the user that is detected by the movement sensor 170. In one embodiment, the movement sensor 170 is an accelerometer sensor (such as a MEMS accelerometer) and the movement data 136 is (or includes) acceleration data, which corresponds to acceleration of the user in at least one direction. Accordingly, the movement sensor 170 is configured to generate movement data 136 that corresponds to acceleration of the user as the user is moving. The movement sensor 170 is provided as any type of sensor configured to generate the movement data 136, such as at least one single-axis or a multi-axis microelectromechanical (MEMS) accelerometer, a gyroscope, and/or a magnetometer.

The transceiver 174 of the monitoring device 104, which is also referred to as a wireless transmitter and/or receiver, is configured to transmit and to receive data from the personal electronic device 108. In one embodiment, the transceiver 174 is configured for operation according to the Bluetooth® wireless data transmission standard. In other embodiments, the transceiver 174 comprises any desired transceiver configured to wirelessly transmit and receive data using a protocol including, but not limited to, Near Field Communication ("NFC"), IEEE 802.11, Global System for Mobiles ("GSM"), and Code Division Multiple Access ("CDMA").

The memory 178 of the monitoring device 104 is an electronic data storage unit, which is also referred to herein as a non-transient computer readable medium. The memory 178 is configured to store the movement data 136, program instruction data 186, user parameter data 244, and any other electronic data associated with the fitness tracking system 100. The program instruction data 186 includes computer executable instructions for operating the monitoring device 104.

The controller 182 of the monitoring device 104 is configured to execute the program instruction data 186 for controlling the movement sensor 170, the transceiver 174, and the memory 178. Accordingly, the controller 182 is configured to sample and store the movement data 136 generated by the movement sensor 170. The controller 182 is further configured to execute the program instruction data 186 to determine and/or calculate the user parameter data 244 by applying, for example, a set of rules to the movement data 136. As described in further detail herein, the user parameter data 244 includes at least a number of steps, a step time, a ground contact time, a number of strides, a stride length, a stride time, a speed, a distance, a cadence, and ratios of these parameters. The controller 182 is configured as a microprocessor, a processor, or any other type of electronic control chip.

The battery 184 is configured to supply the movement sensor 170, the transceiver 174, the memory 178, and the controller 182 with electrical energy. In one embodiment, the battery 184 is a button cell battery or a coin cell battery that is permanently embedded in the monitoring device 104 and/or the shoe 150, such that the battery 184 is not user accessible and cannot be replaced or recharged without destroying at least one of the shoe 150 and the monitoring device 104. In another embodiment, the battery 184 is a user-accessible rechargeable lithium polymer battery that is configured to be recharged and/or replaced by the user.

The Personal Electronic Device

Figure 3:
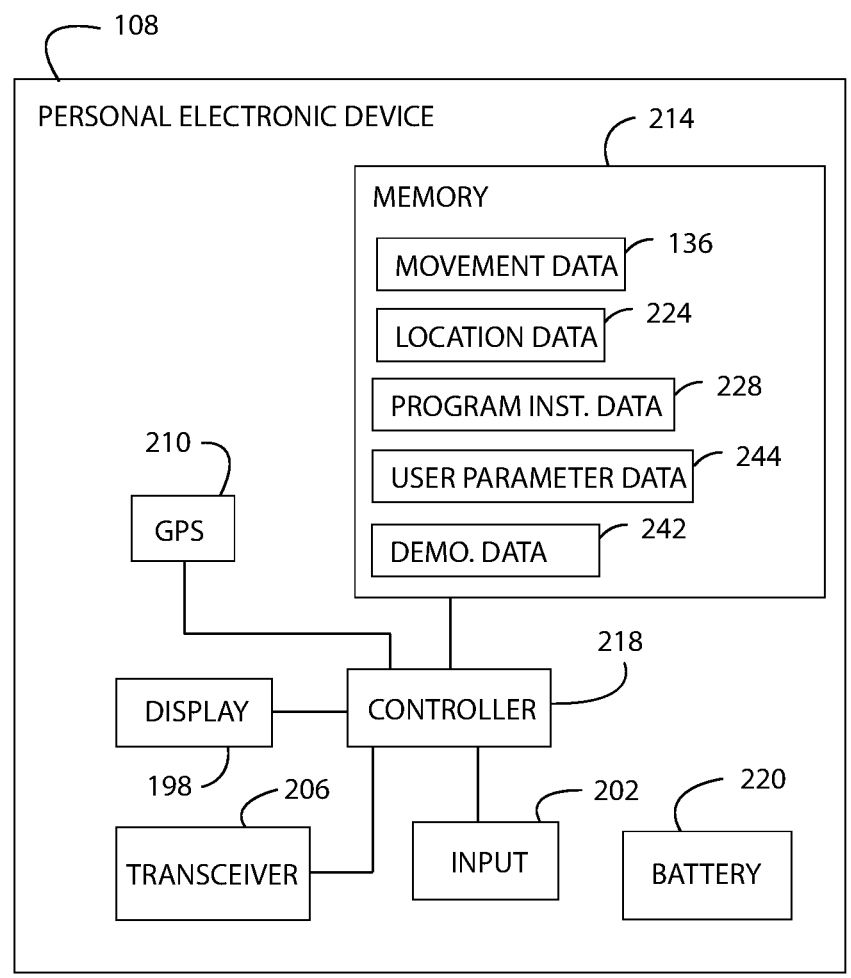
FIG. 3 is a block diagram of the personal electronic device of the fitness tracking system shown in FIG. 1.

As shown in FIG. 3, the personal electronic device 108 is configured as a smartphone. The personal electronic device 108 is configured for wireless communication with the monitoring device 104 and the remote processing server 112. In other embodiments, the personal electronic device 108 is provided as a smartwatch, an electronic wristband, or the like.

The personal electronic device 108 includes display unit 198, an input unit 202, a transceiver 206, a GPS receiver 210, and a memory 214 each of which is operably connected to a processor or a controller 218 and a battery 220. The display unit 198 is configured as a liquid crystal display (LCD) panel configured to display static and dynamic text, images, and other visually comprehensible data based on at least the movement data 136. For example, the display unit 198 is configurable to display one or more interactive interfaces or display screens including, but not limited to, a distance traversed by the user, a speed of the user, and a stride length of the user. The display unit 198, in another embodiment, is any display unit as desired by those of ordinary skill in the art.

The input unit 202 of the personal electronic device 108 is configured to receive input data from a user. The input unit 202 may be configured as a touchscreen applied to the display unit 198 that is configured to enable a user to supply input data via the touch of a finger and/or a stylus. In another embodiment, the input unit 202 comprises any device configured to receive input data, as may be utilized by those of ordinary skill in the art, including, for example, one or more buttons, switches, keys, microphones, cameras, and/or the like.

With continued reference to FIG. 3, the transceiver 206 of the personal electronic device 108 is configured to communicate wirelessly with the transceiver 174 of the monitoring device 104 and the remote processing server 112. The transceiver 206 wirelessly communicates with the remote processing server 112 either directly or indirectly via the cellular network 128 (FIG. 1), a wireless local area network ("Wi-Fi"), a personal area network, and/or any other wireless network over the Internet 124. Accordingly, the transceiver 206 is compatible with any desired wireless communication standard or protocol including, but not limited to, Near Field Communication ("NFC"), IEEE 802.11, Bluetooth®, Global System for Mobiles ("GSM"), and Code Division Multiple Access ("CDMA"). The transceiver 206 is configured to wirelessly transmit and receive data from the remote processing server 112, and to wirelessly transmit and receive data from the monitoring device 104.

The GPS receiver 210 of the personal electronic device 108 is configured to receive GPS signals from the GPS 132 (FIG. 1). The GPS receiver 210 is further configured to generate location data 224 that is representative of a current location on Earth of the personal electronic device 108 based on the received GPS signals. The location data 224, in one embodiment, includes latitude and longitude information. The controller 218 is configured to store the location data 224 generated by the GPS receiver 210 in the memory 214.

As shown in FIG. 3, the memory 214 of the personal electronic device 108 is an electronic data storage unit, which is also referred to herein as a non-transient computer readable medium. The memory 214 is configured to store electronic data associated with operating the personal electronic device 108 and the monitoring device 104 including all or a subset of the movement data 136, the location data 224, program instruction data 228 including computer executable instructions for operating the personal electronic device, demographic data 242, and the user parameter data 244.

The demographic data 242 stored in the memory 214 is based on demographic information of the user and may include gender, height, weight, body mass index ("BMI"), and age, among other data. Any other user demographic, profile, and/or psychographic data may be included in the demographic data 242. Typically, the user supplies the personal electronic device 108 with the information that is stored as the demographic data 242.

The controller 218 of the personal electronic device 108 is configured to execute the program instruction data 228 in order to control the display unit 198, the input unit 202, the transceiver 206, the GPS receiver 210, and the memory 214. The controller 218 is also configured to execute the program instruction data 228 to determine and/or to calculate the user parameter data 244 by applying, for example, the set of rules to the movement data 136. The controller 218 is provided as a microprocessor, a processor, or any other type of electronic control chip.

The battery 220 is configured to supply the display unit 198, the input unit 202, the transceiver 206, the GPS 210, the memory 214, and the controller 218 with electrical energy. In one embodiment, the battery 220 is a rechargeable lithium polymer battery that is configured to be recharged by the user.

The Remote Processing Server

As shown in FIG. 1, the remote processing server 112 is remotely located from the monitoring device 104 and the personal electronic device 108. The server 112 is located at a server physical location and the personal electric device 108 and the monitoring device 104 are located at one or more other physical locations that are different from the server physical location.

The server 112 includes a transceiver 252 and a memory 256 storing at least a portion of the movement data 136, program instructions 260, and at least a portion of the user parameter data 244. Each of the transceiver 252 and the memory 256 is operably connected to a central processing unit ("CPU") 264.

The transceiver 252 of the remote processing server 112 is configured to wirelessly communicate with the personal electronic device 108 either directly or indirectly via the cellular network 128, a wireless local area network ("Wi-Fi"), a personal area network, and/or any other wireless network. Accordingly, the transceiver 252 is compatible with any desired wireless communication standard or protocol including, but not limited to, Near Field Communication ("NFC"), IEEE 802.11, Bluetooth®, Global System for Mobiles ("GSM"), and Code Division Multiple Access ("CDMA").

The CPU 264 of the remote processing server 112 is configured to execute the program instruction data 260 to determine and/or to calculate the user parameter data 244 by applying, for example, the set of rules to the movement data 136. The rules of the set of rules are categorized as mathematical operations, event-specific operations, and processed signals. The CPU 264 is provided as a microprocessor, a processor, or any other type of electronic control chip. Typically, the CPU 264 is more powerful than the controller 218 of the personal electronic device 108 and the controller 182 of the monitoring device 104, thereby enabling the remote processing server 112 to generate the user parameter data 244 more quickly than the devices 104, 108. In some embodiments of the fitness tracking system 100 the remote processing server 112 is not included and/or is not used.

Method of Operation

Figure 4:
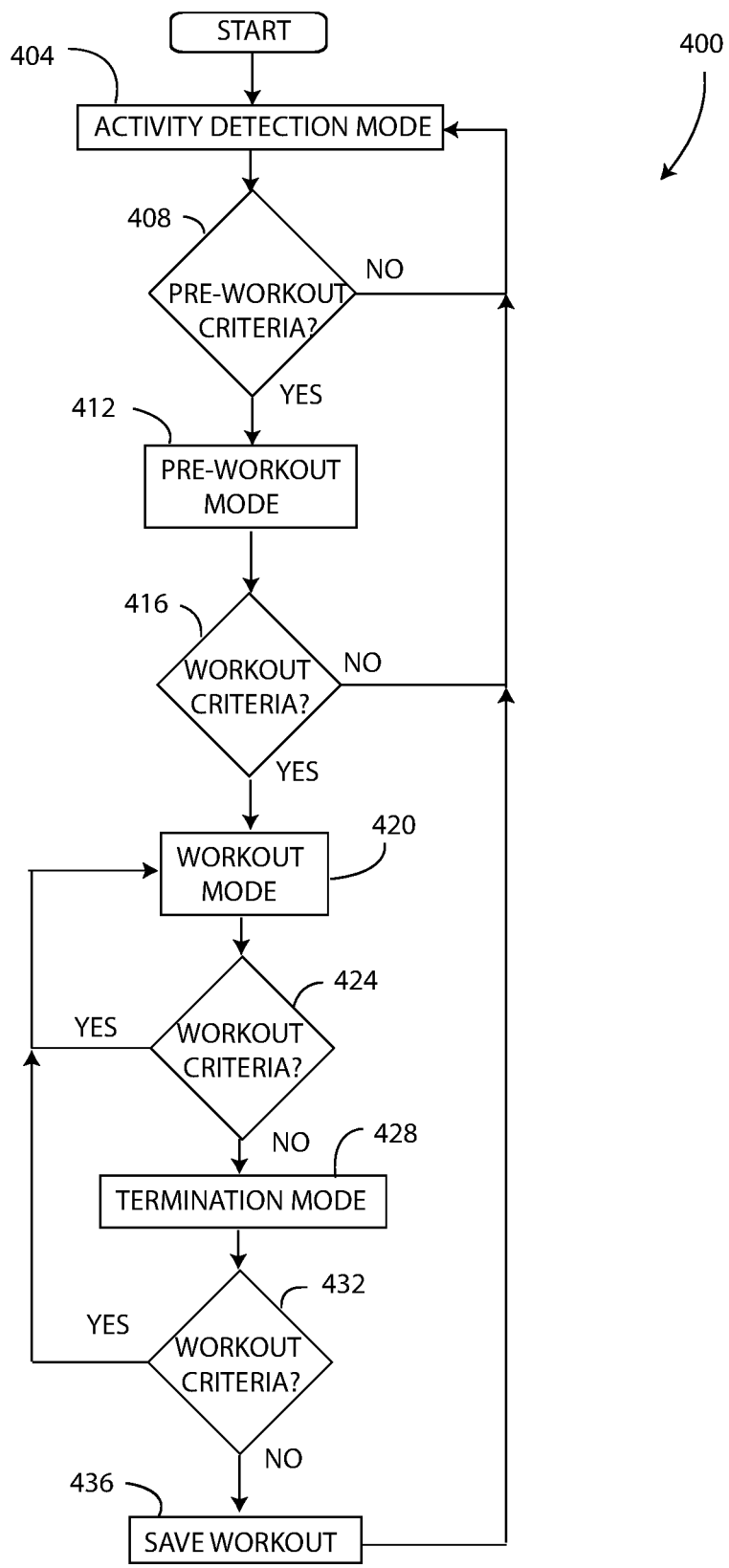
FIG. 4 is a flowchart illustrating an exemplary method of operating the fitness tracking system shown in FIG. 1.

As shown in the flowchart of FIG. 4, the fitness tracking system 100 is configured to execute a method for automatically determining if the system 100 should be operated in an activity detection mode, a pre-workout mode, or a workout mode. The terms "workout" and "workout activity," as used herein, refer to any activity that the user desires the fitness tracking system 100 to generate and to store the user parameter data 244 for later evaluation and review by the user. Exemplary workouts include hiking, running, jogging, walking, and the like. A workout is distinguished herein from a non-workout. The terms "non-workout" and "non-workout activity" as used herein, refer a state of the user when the user is not engaged in a workout and the user does not desire the fitness tracking system 100 to store the user parameter data 244 for later evaluation and review. Exemplary non-workouts include sitting down, lying down, sleeping, standing still. Moreover, non-workout activity includes activity performed at less than a workout pace, for less than a workout distance, and/or for less than a workout duration. An exemplary workout pace is greater than or equal to two miles per hour, an exemplary workout distance is greater than or equal to five hundred feet, an exemplary workout duration is greater than or equal to thirty seconds. Furthermore, non-workout activity includes any intentional or unintentional movement of the movement sensor 170 as may occur during transport of the monitoring device 104 or repositioning of the monitoring device 104.

As shown in block 404, the method 400 includes operating the fitness tracking system 100 in the activity detection mode. In the activity detection mode, the monitoring device 104 enables the movement sensor 170 to generate a data signal corresponding to the movements of the user and/or to the movements of the monitoring device 104. The controller 182 samples the data signal generated by the movement sensor 170, and stores the data in the memory 178 as the movement data 136. In some embodiments, prior to sampling the data signal, the data signal is filtered or smoothed. In other embodiments, the raw data signal is sampled. Moreover, if the personal electronic device 108 is within range, then the monitoring device 104 may wirelessly transmit at least a portion of the movement data 136 to the personal electronic device 108. The personal electronic device 108 stores the movement data 136 in the memory 214. Still further, the personal electronic device 108 may transfer at least a portion of the movement data 136 to the remove processing server 112 to be stored in the memory 256. Prior to operating in the activity detection mode, the fitness tracking system 100 may be operated in a low-power sleep mode in which the movement sensor 170 does not generate the data signal corresponding to the movements of the user. Movement of the monitoring device 104 and/or the personal electronic device 108 "wakes" the fitness tracking system 100 and causes the system 100 to operate in the activity detection mode.

In the activity detection mode, the fitness tracking system 100 samples the data signal generated by the movement sensor 170 at an activity sampling rate (i.e. a first sampling rate or a low sampling frequency). For example, the controller 182 samples the data signal from the movement sensor 170 to generate a plurality of movement data points, which are logged in the memory 178 as the movement data 136. The activity sampling rate is, for example, 12.5 Hz. In other embodiments, the activity sample rate during the activity detection mode is from 5 Hz to 50 Hz. The activity sampling rate is selected to cause the fitness tracking system 100 to consume a comparatively low amount of electrical energy and is a means of power savings. The movement data 136 that is logged during the activity detection mode is also referred to herein as the "first sampled data." The term "first sampled data," as used herein, corresponds to the movement data 136 stored in the memory 178 during the activity detection mode. The "first sampled data" is sampled at the activity sampling rate.

In the activity detection mode, the fitness tracking system 100 stores the movement data 136 for a buffer predetermined time period (i.e. a first predetermined time period) according to a first in first out ("FIFO") data storage approach. The buffer predetermined time period is, for example, twelve seconds. In other embodiments, the buffer predetermined time period is from five to thirty seconds. The buffer predetermined time period is selected to cause the fitness tracking system 100 to utilize only a small portion of the capacity of the memory 178 and to consume a low amount of electrical energy and, therefore, is a means of power savings.

The fitness tracking system 100 operates in the activity detection mode in response to passive user actions. For example, the user may have put on the shoe 150 that includes the monitoring device 104, which is a passive user action that is detectable by the movement sensor 170. Additionally or alternatively, the fitness tracking system 100 starts operating in the activity detection mode after the user has stood up or started walking after a period of inactivity. The user actions are described as "passive" actions, because the user has not provided the fitness tracking system 100 with an active input. As used herein, an "active input" is an input by the user using the input unit 202. The movement sensor 170 detects passive user actions having a magnitude equal to or exceeding a predetermined threshold. For example, when the user is not wearing the shoe 150, gently moving the shoe 150 from one position to another does not result in movement having a magnitude that exceeds the predetermined threshold, so as to conserve electrical energy. Whereas, the user inserting her foot into the shoe 150 and tying the shoelaces typically results in movement having a magnitude equal to or in excess of the predetermined threshold.

In the activity detection mode, the fitness tracking system 100 processes the movement data 136 to generate the user parameter data 244 corresponding to movements of the user. Typically, in the activity detection mode, the monitoring device 104 applies the set of rules to the movement data 136 to determine the user parameter data 244. In other embodiments, however, any one or more of the monitoring device 104, the personal electronic device 108, and the remote processing server 112 determines the user parameter data 244 when the fitness tracking system 100 is operated in the activity detection mode. The rules of the set of rules are categorized as mathematical operations, event-specific operations, and processed signals. Moreover, in one embodiment, the twelve second buffer of movement data 136 generated in the activity detection mode is continually processed to generate the user parameter data 244. Only the user parameter data 244 corresponding to the most recent twelve seconds of movement data 136 is stored in the memory 178 during the activity detection mode.

The user parameter data 244 includes parameters such as number of steps, step time, ground contact time, number of strides, stride length, stride time, speed, distance, cadence, and ratios including these parameters. The number of steps is a count of the number of footsteps taken by the user. The step time is a duration of time between consecutive footsteps of the user. The step time is stored as a list of step times and/or an average step time. The ground contact time is a duration of time that the user's foot is contact with the ground as the user performs bipedal movement. The ground contact time is stored as a list of measured ground contact times and/or an average ground contact time. The number of strides is a count of the number of strides taken by the user. The stride length is a distance corresponding to a length of a stride taken by the user. The stride length is stored as a list of measured stride lengths and/or an average stride length. The stride time is a duration of time corresponding to each stride taken by the user. The stride time is stored as a list of stride times and/or an average stride time. The speed corresponds to the ground speed of the user. The speed is stored as a list of instantaneous speeds and/or an average speed. The distance corresponds to a distance traversed by the user. The cadence corresponds to number of strides taken per time period of the user and/or the number of steps taken per time period by the user. For example, cadence is determined in steps per minute or strides per minute. Cadence may also be determined as an instantaneous cadence and/or an average cadence.

Additional user parameters may also be stored as the user parameter data 244 that are based on the demographic data 242 and/or based on ratios of the aforementioned user parameters. For example, ratios of ground contact time/stride time, stride length/height of the user, and step length/height may be stored as the user parameter data 244. Moreover, variables such as peak acceleration and RMS acceleration may be also calculated from the movement data 136 and stored as the user parameter data 244.

Accordingly, during the activity detection mode of block 404, at least one of the personal electronic device 108, the monitoring device 104, and the remote processing server 112 calculates the user parameter data 244 based on the twelve seconds of buffered activity movement data 136. The user parameter data 244 is stored in at least one of the memories 178, 214, 256.

Next, in block 408 of the method 400, the fitness tracking system 100 applies pre-workout criteria to the user parameter data 244 that were calculated during the activity detection mode of block 404 to determine if the fitness tracking system 100 should continue operating in the activity detection mode or change to the pre-workout mode. The pre-workout criteria are selected to enable the fitness tracking system 100 to determine if the user is engaged in a workout or if the user is engaged in a non-workout activity.

In an exemplary comparison at block 408, the number of strides stored as at least part of the user parameter data 244 is compared to a pre-workout stride threshold. If the number of detected strides satisfies the pre-workout stride threshold, then the fitness tracking system 100 switches from operating in the activity detection mode to operating in the pre-workout mode of block 412. Whereas, if the number of detected strides does not satisfy the pre-workout stride threshold, the fitness tracking system 100 continues to operate in the activity detection mode. As used herein, a threshold may be "satisfied" by a value that is lower than, higher than, or equal to the threshold. Unless specified, there are no constraints, numerical or otherwise, on the thresholds or the values compared to the thresholds. For example, in one embodiment, the pre-workout stride threshold is fifteen strides. If the number of strides is greater than or equal to the pre-workout stride threshold, then the pre-workout stride threshold is satisfied, and the fitness tracking system 100 switches from operating in the activity detection mode to operating in the pre-workout mode of block 412. If the number of strides is less than the pre-workout stride threshold, then the pre-workout stride threshold is not satisfied and the fitness tracking system 100 continues to operate in the activity detection mode of block 404. The pre-workout stride threshold is based on any one or more of the user parameters of the user parameter data 244. The comparison of block 408 is made by at least one of the monitoring device 104, the personal electronic device 108, and the remote processing server 112.

In another example, if the user wears the shoe 150 including the monitoring device 104 and takes at least fifteen strides during the buffer predetermined time period then fitness tracking system 100 determines at block 408 that the pre-workout criteria have been met and the fitness tracking system 100 changes operating modes from the activity detection mode to the pre-workout mode. Whereas, for example, if the user wears the shoe 150 including the monitoring device 104 and takes less than fifteen strides during the buffer predetermined time period then the fitness tracking system 100 determines at block 408 that the pre-workout criteria have not been met and the fitness tracking system 100 continues to operate in the activity detection mode.

In block 412, the fitness tracking system 100 is operated in the pre-workout mode. In the pre-workout mode, the monitoring device 104 continues to enable the movement sensor 170 to generate the data signal corresponding to the movements of the user. The monitoring device 104 samples the data signal, and stores the sampled data in the memory 178 as the movement data 136. Moreover, if the personal electronic device 108 is within range, then the monitoring device 104 transmits at least a portion of the movement data 136 to the personal electronic device 108. The personal electronic device 108 stores the movement data 136 in the memory 214. The personal electronic device 108 may transmit the movement data 136 to the remote processing server 112, which stores the movement data 136 in the memory 256.

As compared to the activity detection mode in the pre-workout mode, the fitness tracking system 100 samples the data signal generated by the movement sensor 170 at a higher workout sampling rate (i.e. a second sampling rate or a high sampling frequency) instead of the activity sampling rate. The workout sampling rate is greater than the activity sampling rate. In the pre-workout mode, the movement sensor 170 generates the data signal corresponding to the movements of the user, and the controller 182 samples the data signal at the workout sampling rate to generate additional movement data points, which are stored in the memory 178 as the movement data 136 (i.e. second sampled data). The workout sampling rate is, for example, 200 Hz. In other embodiments, the workout sample rate is from 100 Hz to 500 Hz. The workout sampling rate is selected to cause the fitness tracking system 100 to accurately generate data that corresponds to the movement of the user. When operated at the workout sampling rate, the fitness tracking system 100 consumes comparatively more electrical energy than when the fitness tracking system 100 is operated at the activity sampling rate. The term "second sampled data," as used herein, corresponds to the movement data 136 stored in the memory 178 during the pre-workout mode and the workout mode. The "second sampled data" is sampled at the workout sampling rate. The second sampled data is different from the first sampled data.

All or most of the movement data 136 collected during the pre-workout mode is stored in the memory 178. In comparison, only the newest data (i.e. data that was generated no longer ago than the duration of the buffer predetermined time period) is stored in the memory 178 during the activity detection mode. Accordingly, operating the fitness tracking system 100 in the pre-workout mode uses a greater amount of memory capacity than the amount of memory capacity used to operate the fitness tracking system 100 in the activity detection mode. Moreover, in the pre-workout mode, the fitness tracking system 100 may be configured to generate additional user parameter data 244 as compared to the number of parameters generated during the activity detection mode. For example, in the activity detection mode, the fitness tracking system 100 may be configured to generate user parameter data 244 pertaining to only the number of strides taken. Whereas, in the pre-workout mode all of the available user parameter data 244 parameters are generated. The fitness tracking system 100 overwrites the user parameter data 244 generated during the activity detection mode with the user parameter data 244 generated during the pre-workout mode.

Next, in block 416 of the method 400, the fitness tracking system 100 applies an iterative workout criteria process to the user parameter data 244 calculated during the pre-workout mode of block 412, to determine if the fitness tracking system 100 should revert to operating in the activity detection mode or change to operating in the workout mode. Typically, the fitness tracking system 100 is operated in the pre-workout mode for a pre-workout predetermined time period (i.e. a second predetermined time period or a pre-workout time window) before applying the process in block 416. The pre-workout predetermined time period is of a duration suitable for generating meaningful user parameter data 244 based on the movement data 136 of the pre-workout mode. An exemplary pre-workout predetermined time period is thirty seconds. The pre-workout predetermined time period may range from fifteen seconds to three minutes. Typically, the movement data 136 is logged for a longer time period in the pre-workout mode than in the activity detection mode. As explained below, the iterative process applied in block 416 enables the fitness tracking system 100 to determine automatically (i.e. without an active input from the user) if the user is engaged in a workout or if the user is engaged in a non-workout activity.

Figure 5:
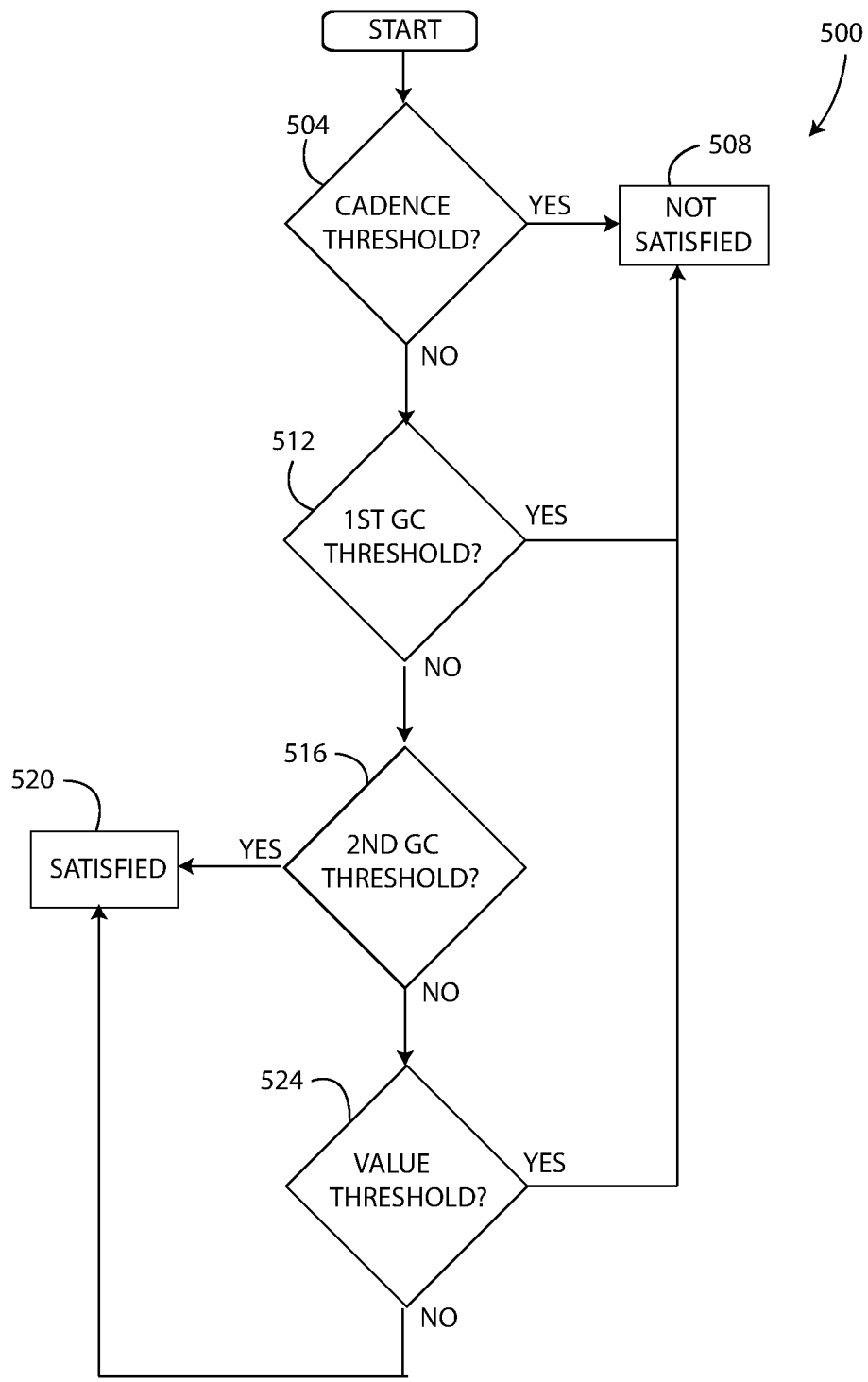
FIG. 5 is a flowchart illustrating an exemplary process applied by the fitness tracking system for determining if workout criteria have been satisfied.

FIG. 5 is a flowchart illustrating a first exemplary iterative process 500 applied at block 416 of FIG. 4. In FIG. 5, the following criteria are iteratively applied to the user parameter data 244 generated during the pre-workout mode. The criteria are applied by any one or more of the controller 182, the controller 218, and the CPU 264. First, as shown in block 504, the cadence of the user is compared to a cadence threshold. If the cadence of the user satisfies the cadence threshold, then the workout criteria have not been met (i.e. not satisfied), as shown in block 508. Whereas, if the cadence of the user does not satisfy the cadence threshold, the next criterion is evaluated. As stated above, a threshold may be "satisfied" by a value that is lower than, higher than, or equal to the threshold. In one embodiment, the cadence threshold is selected such that if the user parameter data 244 indicates that the user is exhibiting a cadence less than or equal to the cadence threshold, then the user tends to be engaged in a non-workout activity. The cadence threshold is typically from twenty to one hundred strides per minute and may be based on the demographic data 242. An exemplary cadence threshold is sixty strides per minute, and if the cadence of the user is less than or equal to the cadence threshold, then the cadence threshold is satisfied and the workout criteria have not been met, as shown in block 508. Whereas, if the cadence of the user is greater than the cadence threshold, the cadence threshold is not satisfied and the next criterion is evaluated.

In block 512, a ground contact value of the user is compared to a first ground contact threshold. As used herein, the ground contact value encompasses at least the ground contact time of the user and/or a ground contact time percentage of the user. Moreover, as used herein, the ground contact threshold encompasses a time threshold based on the ground contact time and/or a percentage threshold based on the ground contact time percentage. In the example of block 512, if the ground contact value satisfies the first ground contact threshold, then the workout criteria have not been met, as shown in block 508. Whereas, if the ground contact value does not satisfy the first ground contact threshold, the next criterion is evaluated. In an example, the ground contact value is the ground contact time of the user and the first ground contact threshold is a first time threshold. The first time threshold is from 200 ms to 800 ms and may be based on the demographic data 242. An exemplary first time threshold is 600 ms. In this example, if the ground contact time of the user is greater than or equal to the first time threshold, then the first time threshold is satisfied and the workout criteria have not been met, as shown in block 508. Whereas, if the ground contact time of the user is less than the first time threshold, then the first time threshold is not satisfied and the next criterion is evaluated. The first time threshold is typically selected such that if after evaluating the criterion of block 504, the user parameter data 244 indicates that the user is exhibiting a ground contact time greater than or equal to the first time threshold, then the user tends to be engaged in a non-workout activity.

Next, in block 516 the ground contact value is compared to a second ground contact threshold. If the ground contact value satisfies the second ground contact threshold, then the workout criteria have been met, as shown in block 520. Whereas, if the ground contact value does not satisfy the second ground contact threshold, the next criterion is evaluated. In an example, the ground contact value is the ground contact time of the user and the second ground contact threshold is a second time threshold. The second time threshold is from 200 ms to 800 ms and may be based on the demographic data 242. An exemplary second time threshold is 400 ms. If the ground contact time of the user is less than or equal to the second time threshold, then the second ground contact threshold is satisfied and the workout criteria have been met, as shown in block 520. Whereas, if the ground contact time of the user is greater than the second time threshold, then the second ground contact threshold is not satisfied and the next criterion is evaluated. The second time threshold is typically selected such that if after evaluating the criteria of blocks 504 and 512, the user parameter data 244 indicates that the user is exhibiting a ground contact time less than or equal to the second time threshold, then the user tends to be engaged in a workout activity.

In block 524, a function value is calculated from a function and the function value is compared to a value threshold. The function is stored in at least one of the memories 178, 214, 256. The function is a relationship including at least one parameter of the user parameter data 244 and may be based on the demographic data 242. The function value is calculated by applying at least a portion of the user parameter data 244 to the function. An exemplary function is a product of the cadence of the user plus forty-five and the ground contact time of the user. (i.e. (45+Cadence)*Ground Contact Time). If the function value satisfies the value threshold, then the workout criteria have not been met, as shown in block 508. Whereas, if the function value does not satisfy the value threshold, then the workout criteria have been met, as shown in block 520. In an example, if the function value is greater than or equal to the value threshold, then the function value satisfies the value threshold and the workout criteria have not been met, as shown in block 508. If the function value is less than the value threshold, then the function value does not satisfy the value threshold and the workout criteria are satisfied, as shown in block 520. The value threshold is typically selected such that if after evaluating the criteria of blocks 504, 512, and 516, the function value satisfies the value threshold, then the user tends to be engaged in a non-workout activity.

Figure 6:
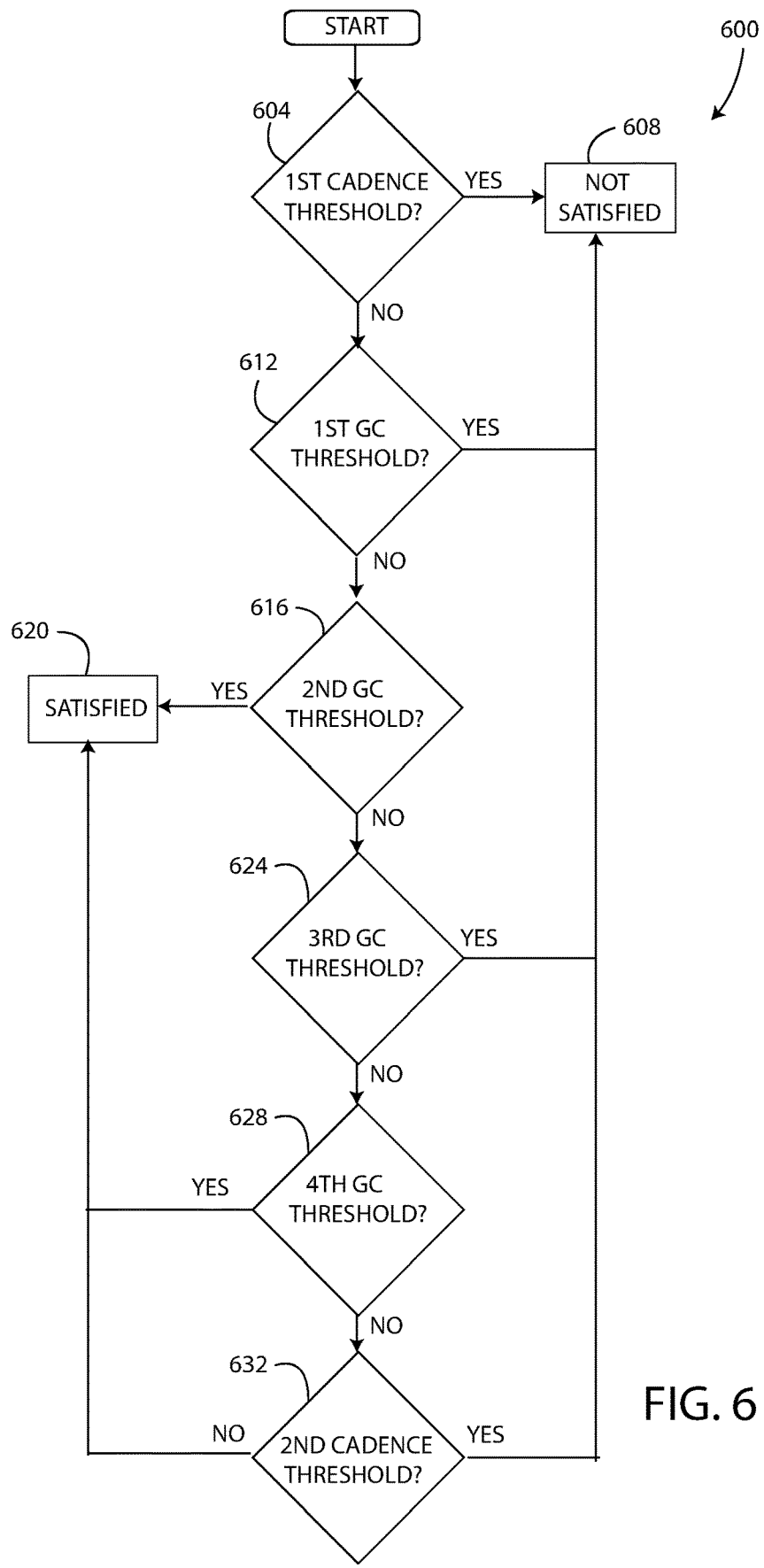
FIG. 6 is a flowchart illustrating another exemplary process applied by the fitness tracking system for determining if the workout criteria have been satisfied.

FIG. 6 is a flowchart illustrating a second exemplary iterative process 600 applied at block 416 of the flowchart of FIG. 4. In FIG. 6, the following criteria are iteratively applied to the user parameter data 244 generated during the pre-workout mode. The criteria are applied by any one or more of the controller 182, the controller 218, and the controller 264. First, as shown in block 604, the cadence of the user is compared to a first cadence threshold. If the cadence of the user satisfies the first cadence threshold, then the workout criteria have not been met, as shown in block 608. As stated above, a threshold may be "satisfied" by a value that is lower than, higher than, or equal to the threshold. Whereas, if the cadence of the user does not satisfy the first cadence threshold, the next criterion is evaluated. The first cadence threshold is typically selected such that if the user parameter data 244 indicates that the user is exhibiting a cadence less than or equal to the first cadence threshold, then the user tends to be engaged in a non-workout activity. The first cadence threshold is from twenty to one hundred strides per minute and may be based on the demographic data 242. For example, a fit person (based on the demographic data 242) tends to have a higher cadence threshold than a less fit person (based on the demographic data 242). An exemplary first cadence threshold is sixty strides per minute. In this example, if the cadence of the user is less than or equal to the first cadence threshold, then the cadence of the user satisfies the first cadence threshold and the workout criteria have not been met, as shown in block 608. Whereas, if the cadence of the user is greater than the first cadence threshold, then the cadence of the user does not satisfy the first cadence threshold and the next criterion is evaluated.

In block 612, a first ground contact value is compared to a first ground contact threshold. If the first ground contact value satisfies the first ground contact threshold, then the workout criteria have not been met, as shown in block 608. Whereas, if the first ground contact value does not satisfy the first ground contact threshold, then the next criterion is evaluated. In the example of FIG. 6, the first ground contact value is the ground contact time of the user and the first ground contact threshold is a first time threshold. The first time threshold is from 200 ms to 800 ms and may be based on the demographic data 242. An exemplary first time threshold is 600 ms. If the ground contact time of the user is greater than or equal to the first time threshold, then the first ground contact threshold is satisfied and the workout criteria have not been met, as shown in block 608. Whereas, if the ground contact time of the user is less than the first time threshold, then the first ground contact threshold is not satisfied and the next criterion is evaluated. The first time threshold is typically selected such that if after evaluating the criteria of block 604, the user parameter data 244 indicates that the user is exhibiting a ground contact time greater than or equal to the first time threshold, then the user tends to be engaged in a non-workout activity.

Next, in block 616 the first ground contact value is compared to a second ground contact threshold. If the first ground contact value satisfies the second ground contact threshold, then the workout criteria are satisfied, as shown in block 620. Whereas, if the first ground contact value does not satisfy the second ground contact threshold, then the next criterion is evaluated. In the example of FIG. 6, the first ground contact value is, as described above, the ground contact time of the user, and the second ground contact threshold is a second time threshold. The second time threshold is typically from 200 ms to 800 ms and may be based on the demographic data 242. An exemplary second time threshold is 400 ms. If the ground contact time of the user is less than or equal to the second time threshold, then the second ground contact threshold is satisfied and the workout criteria have been met, as shown in block 620. Whereas, if the ground contact time of the user is greater than the second time threshold, then the second ground contact threshold is not satisfied and the next criterion is evaluated. The second time threshold is typically selected such that if after evaluating the criteria of blocks 604 and 612, the user parameter data 244 indicates that the user is exhibiting a ground contact time less than or equal to the second time threshold, then the user tends to be engaged in a workout activity.

In block 624, a second ground contact value is compared to a third ground contact threshold. If the second ground contact value satisfies the third ground contact threshold, then the workout criteria have not been met, as shown in block 608. Whereas, if the second ground contact value does not satisfy the third ground contact threshold, then the next criterion is evaluated. In the example of FIG. 6, the second ground contact value is a ground contact time percentage of the user and the third ground contact threshold is a first ground contact time percentage threshold. As used herein, the ground contact time percentage of the user corresponds to the ground contact time of the user divided by the stride time of the user. The quotient may be multiplied by 100 to arrive at a percentage. The first ground contact time percentage threshold is from 25% to 100% and may be based on the demographic data 242. An exemplary first ground contact time percentage threshold is 65%. In the example of FIG. 6, if the ground contact time percentage of the user is greater than or equal to the first ground contact time percentage threshold, then the second ground contact value satisfies the third ground contact threshold and the workout criteria have not been met, as shown in block 608. Whereas, if the ground contact time percentage of the user is less than the first ground contact time percentage threshold, then the second ground contact value does not satisfy the third ground contact threshold and the next criterion is evaluated. The first ground contact time percentage threshold is typically selected such that if after evaluating the criteria of blocks 604, 612, and 616, the user parameter data 244 indicates that the user is exhibiting a ground contact time percentage greater than or equal to the first ground contact time percentage threshold then the user tends to be engaged in a non-workout activity.

Next, in block 628, the second ground contact value is compared to a fourth ground contact threshold. If the second ground contact value satisfies the fourth ground contact threshold, then the workout criteria have been met, as shown in block 620. Whereas, if the second ground contact value does not satisfy the fourth ground contact threshold, then the next criterion is evaluated. In the example of FIG. 6, the second ground contact value, as described above, is the ground contact time percentage of the user, as determined from the user parameter data 244, and the fourth ground contact threshold is a second ground contact time percentage threshold. The second ground contact time percentage threshold is from 25% to 100% and may be based on the demographic data 242. An exemplary second ground contact time percentage threshold is 45%. If the ground contact time percentage of the user is less than or equal to the second ground contact time percentage threshold, then the second ground contact value satisfies the fourth ground contact threshold and the workout criteria have been met, as shown in block 620. Whereas, if the ground contact time percentage of the user is greater than the second ground contact time percentage threshold, then the second ground contact value does not satisfy the fourth ground contact threshold and the next criterion is evaluated. The second ground contact time percentage threshold is selected such that if after evaluating the criteria of blocks 604, 612, 616, and 624, the user parameter data 244 indicates that the user is exhibiting a ground contact time percentage less than or equal to the second ground contact time percentage threshold then the user tends to be engaged in a workout activity.

In block 632, the cadence of the user is compared to a second cadence threshold. If the cadence of the user satisfies the second cadence threshold, then the workout criteria have not been met, as shown in block 608. Whereas, if the cadence of the user does not satisfy the second cadence threshold, then the workout criteria have been met, as shown in block 620. The second cadence threshold is from fifty to one hundred strides per minutes and may be based on the demographic data 242. An exemplary second cadence threshold is seventy-two strides per minute. If the cadence of the user is less than or equal to the second cadence threshold, then the cadence of the user satisfies the second cadence threshold and the workout criteria have not been met, as shown in block 608. Whereas, if the cadence of the user is greater than the second cadence threshold, then the cadence of the user does not satisfy the second cadence threshold and the workout criteria have been met, as shown in block 620. The second cadence threshold is typically selected such that if after evaluating the criteria of blocks 604, 612, 616, 624, and 628, the user parameter data 244 indicates that the user is exhibiting a cadence less than or equal to the second cadence threshold, then the user tends to be engaged in a non-workout activity.

Figure 7:
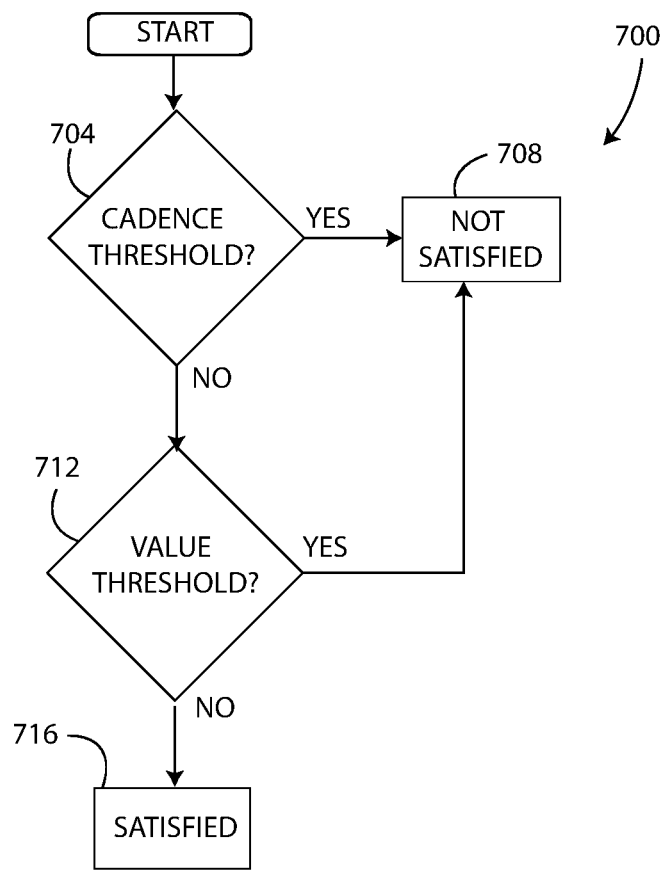
FIG. 7 is a flowchart illustrating a further exemplary process applied by the fitness tracking system for determining if the workout criteria have been satisfied.

FIG. 7 is a flowchart illustrating a third exemplary iterative process 700 applied at block 416 of the flowchart of FIG. 4. In FIG. 7, the following criteria are iteratively applied to the user parameter data 244 generated during the pre-workout mode. The criteria are applied by any one or more of the controller 182, the controller 218, and the controller 264. First, as shown in block 704, the cadence of the user is compared to a cadence threshold. If the cadence of the user satisfies the cadence threshold, then the workout criteria have not been met, as shown in block 708. Whereas, if the cadence of the user does not satisfy the cadence threshold, the next criterion is evaluated. The cadence threshold is typically selected such that if the user parameter data 244 indicates that the user is exhibiting a cadence less than or equal to the cadence threshold, then the user tends to be engaged in a non-workout activity. The cadence threshold is from twenty to one hundred strides per minute and may be based on the demographic data 242. An exemplary cadence threshold is sixty strides per minute. If the cadence of the user is less than or equal to the cadence threshold, then the cadence of the user satisfies the cadence threshold and the workout criteria have not been met, as shown in block 708. Whereas, if the cadence of the user is greater than the cadence threshold, then the cadence of the user does not satisfy the cadence threshold and the next criterion is evaluated.

In block 712, a function value is calculated or determined from a function and the function value is compared to a value threshold. The function is stored in at least one of the memories 178, 214, 256. The function is a relationship including at least one parameter of the user parameter data 244 and may be based on the demographic data 242. The function value is calculated by applying at least a portion of the user parameter data 244 to the function. An exemplary function is a product of the cadence of the user plus forty-five and the ground contact time of the user. (i.e. (45+Cadence)*Ground Contact Time). If the function value satisfies the value threshold, then the workout criteria have not been met, as shown in block 708. Whereas, if the function value does not satisfy the value threshold, then the workout criteria have been met, as shown in block 716. In an example, if the function value is greater than or equal to the value threshold, then the workout criteria are not satisfied, as shown in block 708, and if the function value is less than the value threshold, then the workout criteria are satisfied, as shown in block 716. The value threshold is typically selected such that if after evaluating the criteria of block 704 and the function value is not satisfied, then the user tends to be engaged in a workout activity.

In another embodiment, the function considered at block 712 of FIG. 7 is based only on the ground contact time of the user. Specifically, the ground contact time of the user is applied to the function and the output of the function is compared to a value threshold. If, for example, the output of the function is greater than the value threshold, then the function value satisfies the value threshold. Whereas, if, for example, the output of the function is less than or equal to the value threshold, then the function value does not satisfy the value threshold.

With reference again to the flowchart of FIG. 4, if after applying one of the iterative processes 500, 600, 700 it is determined that the workout criteria have not been satisfied, then the fitness tracking system 100 switches from operating in the pre-workout mode to operating in the activity detection mode. Moreover, the movement data 136 stored during the pre-workout mode is deleted from the memories 178, 214, 256. Whereas, if after applying one of the iterative processes 500, 600, 700 it is determined that the workout criteria have been satisfied, then the fitness tracking system 100 switches from operating in the pre-workout mode to operating in the workout mode of block 420.

In block 420, the fitness tracking system 100 is operated in the workout mode. In the workout mode, the movement sensor 170 continues to generate the data signal corresponding to the movements of the user. The fitness tracking system 100 samples the data signal generated by the movement sensor 170 at the workout sampling rate when operated in the workout mode. The sampled data is saved as the movement data 136 in at least one of the memory 178, the memory 214, and the memory 256. In particular, the movement data 136 is stored in the memory 178, 214, 256 during the workout mode for as long as the fitness tracking system 100 is operated in the workout mode. For example, if the fitness tracking system 100 is operated in the workout mode for thirty minutes, then the corresponding thirty minutes of movement data 136 are saved to the memory 178, 214, 256. Moreover, the movement data 136 stored in the memory 178, 214, 256 during the pre-workout mode are also saved as part of the movement data 136 associated with the workout mode. In this way, movement data 136 associated with the beginning seconds of a workout are not lost in applying the processes 500, 600, 700 used to determine the state of the fitness tracking system 100.

In the workout mode, the fitness tracking system 100 processes the movement data 136 to generate the user parameter data 244 corresponding to movements of the user that have occurred during the time in which the fitness tracking system 100 is operated in the workout mode. Moreover, the user parameter data 244 stored in the memory 178, 214, 256 during the pre-workout mode are also saved as part of the user parameter data 244 associated with the workout mode. In this way, user parameter data 244 associated with the beginning seconds of a workout are not lost in applying the processes 500, 600, 700 used to determine the state of the fitness tracking system 100.

During a workout, the monitoring device 104 is located proximate to the user, whereas the personal electronic device 108 may be left behind or remote to the user during the workout. If the personal electronic device 108 is not carried or worn by the user during the workout, then the personal electronic device 108 may receive the movement data 136 from the monitoring device 104 after the user completes the workout or the next time the two devices 104, 108 are within data transmission range. The personal electronic device 108 may, alternatively, be worn or carried by the user during the workout.

In block 424, during the workout mode, the fitness tracking system 100 applies the workout criteria to the user parameter data 244 using at least one of the processes 500, 600, 700. For example, the fitness tracking system 100 applies the workout criteria to the most recent user parameter data 244 once every second. If the fitness tracking system 100 determines that during the workout mode the workout criteria of the process 500, 600 are satisfied, then the fitness tracking system 100 continues to operate in the workout mode. If, however, the fitness tracking system 100 determines that the workout criteria of the processes 500, 600, 700 are not satisfied, then the fitness tracking system 100 enters the termination mode of block 428.

For example, with reference to FIG. 5, if the user is engaged in a run or a jog with a cadence greater than the cadence threshold (block 504) and a ground contact time less than the first and the second time thresholds (blocks 512 and 516), then the fitness tracking system 100 remains in the workout mode. If, however, at the end of the run or jog, the cadence of the user falls below the first cadence threshold (block 504), then the fitness tracking system 100 detects that the system 100 should not be operated in the workout mode, and the system 100 enters the termination mode because the user may have stopped running or jogging.

In block 428, the fitness tracking system 100 operates in the termination mode. In the termination mode, the movement sensor 170 continues to generate the data signal corresponding to the movements of the user. The fitness tracking system 100 samples the data signal generated by the movement sensor 170 at the workout sampling rate when operated in the termination mode. Moreover, the movement data 136 is saved to at least the memory 178, just as in the workout mode. In the termination mode, the fitness tracking system 100 processes the movement data 136 to generate the user parameter data 244 corresponding to movements of the user that have occurred during the time in which the fitness tracking system 100 is operated in the termination mode.

After entering the termination mode, the fitness tracking system 100 starts a termination predetermined time period. An exemplary termination predetermined time period is five minutes. In other embodiments, the termination predetermined time period is from one minute to ten minutes.

Next, in block 432, as the termination predetermined time period counts down to zero, the fitness tracking system 100 applies at least one of the processes 500, 600, 700 to the most recent thirty seconds of the user parameter data 244 (i.e. a thirty second FIFO buffer of data) and determines if the workout criteria are satisfied. If the workout criteria are satisfied, then the fitness tracking system 100 exits the termination mode and operates again in the workout mode. If, however, the termination predetermined time period elapses without the user parameter data 244 satisfying the workout criteria, then at block 436, the fitness tracking system 100 terminates the workout and stops saving additional movement data 136 and user parameter data 244 in connection with the terminated workout.

For example, the user is engaged in a run or a jog, slows to a walking pace for two minutes to catch her breath, and then continues to run or jog. When the user slows to the walking pace, the fitness tracking system 100 detects at block 424 that the user no longer satisfies the workout criteria and enters the termination mode of block 428. But since the user satisfies the workout criteria again during the termination predetermined time period (i.e. five minutes) by starting to run or jog again after two minutes, the fitness tracking system 100 exits the termination mode and enters the workout mode again.

As another example, the user is engaged in a run or a jog and slows to a slow walking pace for seven minutes. When the user slows to the walking pace, the fitness tracking system 100 detects at block 424 that the user no longer satisfies the workout criteria and enters the termination mode of block 428. At no time during the termination predetermined time period (i.e. five minutes) does the user satisfy the workout criteria. Thus, fitness tracking system 100 has accurately identified the end of the workout and the workout is terminated.

In block 436, the fitness tracking system 100 may assign a date and time to the movement data 136 and user parameter data 244 associated with the terminated workout to assist the user in understanding the saved data. Moreover, the fitness tracking system 100 may display at least some of the movement data 136 and the user parameter data 244 on the display unit 198 of the personal electronic device 108 for viewing by the user.

Also in block 436, the fitness tracking system 100 identifies "termination movement data" and "termination user parameter data" that was stored during the termination predetermined time period. The fitness tracking system 100 deletes from the movement data 136 and the user parameter data 244 the "termination movement data" and the "termination user parameter data" in order to prevent data corresponding to a non-workout activity from corrupting the movement data 136 and the user parameter data 244 from the workout activity. Next, the fitness tracking system 100 operates again in the activity detection mode, as shown in block 404, and the method 400 is repeated.

Advantages of the Fitness Tracking System

As set forth above, the fitness tracking system 100 automatically changes states from the activity detection mode, to the pre-workout mode, to the workout mode, and to the termination mode without requiring the user to identify to the fitness tracking system 100 the type of activity in which the user is engaged. Accordingly, as compared to prior art fitness devices, the fitness tracking system 100 offers many advantages.

In the prior art, the user must provide the fitness device with an input using an input device of the fitness device, such as a button or a touchscreen, to identify to the fitness device that a workout is about to commence. When using the fitness tracking system 100, no such input with the input unit 202 occurs. Instead, the user simply wears at least the monitoring device 104 and then begins the workout at a time of her choosing without any direct inputs to the fitness tracking system 100. The fitness tracking system 100 automatically determines when the workout has begun (by applying the workout criteria of block 416) and saves the movement data 136 and the user parameter data 244 to at least one of the memories 178, 214, 256.

Moreover, in the prior art, the user must provide the fitness device with an input using an input device of the fitness device to identify to the fitness device that the workout has ended. With the fitness tracking system 100, no such input using the input unit 202 occurs. Instead, the user simply stops the workout activity and engages in a non-workout activity. The fitness tracking system 100 automatically detects that the user is not engaged in a workout activity (at block 432) and takes the appropriate steps to terminate the workout session.

Accordingly, unlike the prior art, the fitness tracking system 100 automates the process of starting and stopping the workout data collection process. Such automation, prevents the user from the dealing with the frustration of forgetting to start a fitness device at the beginning of a workout and/or forgetting to stop a fitness device at the end of workout.

The fitness tracking system 100 is a concrete improvement to computer functionality, and the method 400 performed by the fitness tracking system 100 is not a mental process that people go through in their minds. For example, the fitness tracking system 100 samples the movement data 136 at at least two different sampling rates (i.e. the activity sampling rate and the workout sampling rate). Operating at the workout sampling rate is useful for obtaining accurate and meaningful user parameter data 244, but offers more resolution than is needed for the fitness tracking system 100 to determine if the pre-workout criteria have been satisfied (i.e. block 408). Thus, to save power and computing resources (such as memory space), the fitness tracking system 100 operates at the activity sampling rate while in the activity detection mode. Accordingly, the fitness tracking system 100 is an improved computer that automates certain processes for the user and conserves electrical power while doing so. The method 400 of operating the fitness tracking system 100 cannot be performed in the mind of a person.

Saving electrical power when operating the monitoring device 104 increases the service life of the monitoring device 104 and, therefore, improves operation of the monitoring device 104. Specifically, in some embodiments, the battery 184 is permanently embedded in the monitoring device 104 and/or the shoe 150 and cannot be recharged or replaced by the user. The method 400 efficiently uses the electrically energy stored by the battery 184 by operating the monitoring device 104 at the workout sampling rate only when workout activity is occurring.

In another embodiment, the components and functionality of the monitoring device 104 are included in the personal electronic device 108. In such an embodiment, the fitness tracking system 100 does not include the monitoring device 104 and the personal electronic device 108 includes the movement sensor 170 and associated program instruction data 186.

In yet another embodiment, the components and functionality of the monitoring device 104 and the remote processing server 112 are included in the personal electronic device 108. In such an embodiment, the fitness tracking system 100 does not include the monitoring device 104 and the remote processing server 112, and the personal electronic device 108 includes the movement sensor 170 and associated program instruction data 186.

In a further embodiment, the fitness tracking system 100 does not include the personal electronic device 108 and the remote processing server 112, and includes only the monitoring device 104. In such an embodiment, the monitoring device 104 includes all of the components and hardware for performing the method 400 of FIG. 4 and the processes 500, 600, 700 of FIGS. 5-7.

It will be appreciated that the various ones of the foregoing aspects of the present disclosure, or any parts or functions thereof, may be implemented using hardware, software, firmware, tangible, and non-transitory computer readable or computer usable storage media having instructions stored thereon, or a combination thereof, and may be implemented in one or more computer systems.

The above described system and method solves a technological problem common in industry practice related to analysis of collected activity data. Moreover, the above-described system and method improves the functioning of the computer device by verifying collected data against other data for that activity type, while also allowing the user to switch between activities while automatically determining the new activity type.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

It will be apparent to those skilled in the art that various modifications and variations can be made in the disclosed embodiments of the disclosed device and associated methods without departing from the spirit or scope of the disclosure. Thus, it is intended that the present disclosure covers the modifications and variations of the embodiments disclosed above provided that the modifications and variations come within the scope of any claims and their equivalents.

What is claimed is:

1. A fitness tracking system, comprising:
   a shoe;
   a movement sensor mounted to the shoe and configured to generate movement data corresponding to movement of a user; and
   a controller mounted to the shoe and configured to sample the movement data at a first sampling rate as first sampled data when the fitness tracking system is operated in an activity detection mode and to sample the movement data at a second sampling rate as second sampled data when the fitness tracking system is operated in a pre-workout mode or a workout mode,
   wherein the second sampling rate is greater than the first sampling rate, and
   wherein the fitness tracking system is configured to switch from operating in the pre-workout mode to operating in the workout mode in response to a cadence of the user satisfying a cadence condition and a ground contact value of the user satisfying a ground contact condition, wherein the cadence condition is a relationship to a cadence threshold, and the ground contact condition is a relationship to a ground contact threshold, and wherein the fitness tracking system is configured to switch from operating in the pre-workout mode to operating in the workout mode in response to determining that (i) the cadence of the user satisfies the cadence threshold, and (ii) the ground contact value of the user satisfies the ground contact threshold.

2. The fitness tracking system of claim 1, further comprising:
   a monitoring unit including the movement sensor and the controller,
   wherein the monitoring unit is permanently embedded in the shoe such that the monitoring unit cannot be removed from the shoe without destruction thereof.

3. The fitness tracking system of claim 1, further comprising:
   a remote processing server operably connected to the monitoring unit and configured to process the movement data to determine at least one of the cadence of the user and the ground contact value of the user.

4. A method of operating a fitness tracking system, comprising:
   generating movement data corresponding to movement of a user;
   sampling the generated movement data at a first sampling rate as first sampled data when operating the fitness tracking system in an activity detection mode;
   sampling the generated movement data at a second sampling rate as second sampled data when operating the fitness tracking system in a workout mode, wherein the second sampling rate is greater than the first sampling rate;
   operating the fitness tracking system in the activity detection mode in response to determining that a cadence of the user determined from the second sampled data satisfies a cadence threshold;
   operating the fitness tracking system in the activity detection mode in response to determining that (i) the cadence of the user does not satisfy the cadence threshold, and (ii) a ground contact value of the user determined from the second sampled data satisfies a first ground contact threshold; and
   operating the fitness tracking system in the workout mode in response to determining that (i) the cadence of the user does not satisfy the cadence threshold, (ii) the ground contact value of the user does not satisfy the first ground contact threshold, and (iii) the ground contact value of the user satisfies a second ground contact threshold.

5. The method of operating the fitness tracking system of claim 4, further comprising:
   generating the movement data with a monitoring device permanently embedded in a shoe of the user.

6. The method of operating the fitness tracking system of claim 4, further comprising:
   storing the first sampled data for a predetermined time period; and
   storing the second sampled data for a time period that is greater than the predetermined time period.

7. The method of operating the fitness tracking system of claim 6, further comprising:
   determining a number of strides of the user from the first sampled data;
   operating the fitness tracking system in the activity detection mode in response to determining that the determined number of strides of the user does not satisfy a stride threshold;
   operating the fitness tracking system in a pre-workout mode in response to determining that the determined number of strides satisfies the stride threshold; and
   sampling the generated movement data at the second sampling rate as the second sampled data when operating the fitness tracking system in the pre-workout mode.

8. The method of operating the fitness tracking system of claim 4, further comprising:
   after operating the fitness tracking system in the workout mode, switching to operating the fitness tracking system in the activity detection mode in response to determining that the cadence of the user satisfies the cadence threshold for a duration of a termination predetermined time period; and after operating the fitness tracking system in the workout mode, switching to operating the fitness tracking system in the activity detection mode in response to determining that (i) the cadence of the user does not satisfy the cadence threshold, and (ii) the ground contact value of the user satisfies the first ground contact threshold for the duration of the termination predetermined time period.

9. The method of operating the fitness tracking system of claim 8, wherein the termination predetermined time period is five minutes.

10. The method of operating the fitness tracking system of claim 8, further comprising:

after operating the fitness tracking system in the workout mode and then reverting to operating the fitness tracking system in the activity detection mode, deleting movement data of the termination predetermined time period from the second sampled data.

11. The method of operating the fitness tracking of claim 8, further comprising:

operating the fitness tracking system in the activity detection mode in response to determining that (i) the cadence of the user does not satisfy the cadence threshold, (ii) the ground contact value of the user does not satisfy the first ground contact threshold, (iii) the ground contact value of the user does not satisfy the second ground contact threshold, and (iv) a value of a function including the cadence of the user and a ground contact time of the user satisfies a value threshold; and operating the fitness tracking system in the workout mode in response to determining that (i) the cadence of the user does not satisfy the cadence threshold, (ii) the ground contact value of the user does not satisfy the first ground contact threshold, (iii) the ground contact value of the user does not satisfy the second ground contact threshold, and (iv) the value of the function including the cadence of the user and the ground contact time of the user does not satisfy the value threshold.

12. A method of operating a fitness tracking system, comprising:

generating movement data corresponding to movement of a user;

sampling the generated movement data at a first sampling rate as first sampled data when operating the fitness tracking system in an activity detection mode;

sampling the generated movement data at a second sampling rate as second sampled data when operating the fitness tracking system in a pre-workout mode or a workout mode, wherein the second sampling rate is greater than the first sampling rate; and switching from operating the fitness tracking system in the pre-workout mode to operating the fitness tracking system in the workout mode in response to determining that (i) a cadence of the user determined from the second sampled data does not satisfy a cadence threshold, (ii) a ground contact value of the user determined from the second sampled data does not satisfy a first ground contact threshold, and (iii) the ground contact value of the user satisfies a second ground contact threshold.

13. The method of operating the fitness tracking system of claim 12, further comprising:

generating the movement data with a movement sensor embedded in a shoe of the user.

14. The method of operating the fitness tracking system of claim 12, further comprising:

switching from operating the fitness tracking system in the pre-workout mode to the activity detection mode in response to determining that the cadence of the user satisfies the cadence threshold, or (i) the cadence of the user does not satisfy the cadence threshold, and (ii) the ground contact value of the user satisfies the first ground contact threshold.

15. The method of operating the fitness tracking system of claim 12, further comprising:

storing the first sampled data for a predetermined time period; and storing the second sampled data for a time period that is greater than the predetermined time period.

16. The method of operating the fitness tracking system of claim 12, further comprising:

determining a number of strides of the user from the first sampled data; and operating the fitness tracking system in the activity detection mode in response to determining that the determined number of strides of the user does not satisfy a stride threshold; and operating the fitness tracking system in the pre-workout mode in response to determining that the determined number of strides of the user satisfies the stride threshold.

17. The method of operating the fitness tracking system of claim 12, further comprising:

after operating the fitness tracking system in the workout mode, switching to operating the fitness tracking system in the activity detection mode in response to determining that the cadence of the user satisfies the cadence threshold for a duration of a termination predetermined time period, or (i) the cadence of the user does not satisfy the cadence threshold, and (ii) the ground contact value of the user satisfies the first ground contact threshold for the duration of the termination predetermined time period.

18. The method of operating the fitness tracking system of claim 17, further comprising:

after operating the fitness tracking system in the workout mode and then switching to operating the fitness tracking system in the activity detection mode, deleting movement data of the termination predetermined time period from the second sampled data.

19. The method of operating the fitness tracking system of claim 12, further comprising:

switching from operating the fitness tracking system in the pre-workout mode to operating the fitness tracking system in the workout mode in response to determining that (i) the cadence of the user does not satisfy the cadence threshold, (ii) the ground contact value of the user does not satisfy the first ground contact threshold, (iii) the ground contact value of the user does not satisfy the second ground contact threshold, and (iv) a value of a function including the cadence of the user and a ground contact time of the user does not satisfy a value threshold.

* * * * *